United States Patent
Tets et al.

(10) Patent No.: US 7,557,116 B2
(45) Date of Patent: Jul. 7, 2009

(54) SUBSTANCE WHICH EXHIBITS ANTIVIRAL AND ANTIBACTERIAL ACTIVITY AND IS BASED ON DERIVATIVES OF 2,8-DITHIOXO-1H-PYRANO[2,3D 6,5-D']DIPYRIMIDYNE AND 10-AZA-ANALOGUE THEREOF

(76) Inventors: Viktor Veniaminovich Tets, ul. Lensuveta, 27-95, St. Petersburg (RU) 196066; Rimma Iliinichna Ashkinazi, ul. Pushkinskaya, 13-41, St. Petersburg (RU) 191025; Konstantin Andreevich Krasnov, ul. Zheleznovodskaya, 40-20, St. Petersburg (RU) 199155

( * ) Notice: Subject to any disclaimer, the term of this patent is extended or adjusted under 35 U.S.C. 154(b) by 97 days.

(21) Appl. No.: 10/571,652
(22) PCT Filed: Nov. 5, 2003
(86) PCT No.: PCT/RU03/00496

§ 371 (c)(1),
(2), (4) Date: Mar. 10, 2006

(87) PCT Pub. No.: WO2005/026171

PCT Pub. Date: Mar. 24, 2005

(65) Prior Publication Data

US 2007/0037838 A1  Feb. 15, 2007

(30) Foreign Application Priority Data

Sep. 12, 2003  (RU) .............................. 2003128343

(51) Int. Cl.
*A01N 43/54* (2006.01)
*A61K 31/505* (2006.01)
*C07D 239/00* (2006.01)
*C07D 471/00* (2006.01)
*C07D 487/00* (2006.01)
*C07D 491/00* (2006.01)

(52) U.S. Cl. ...................... 514/267; 544/251
(58) Field of Classification Search ................ 544/251; 514/267

See application file for complete search history.

(56) References Cited

U.S. PATENT DOCUMENTS 6,340,755 B1 * 1/2002 Ashkinazi ................... 544/251

OTHER PUBLICATIONS

Pannecouue, et al., New Class of HIV Integrase Inhibitors that Block Viral Replication in Cell Culture, Current Biology, vol. 12, 1169-1177, Jul. 23, 2002.*

* cited by examiner

*Primary Examiner*—James O Wilson
*Assistant Examiner*—Erich A Leeser
(74) *Attorney, Agent, or Firm*—John D. Gueliotta

(57) ABSTRACT

The present invention relates generally to synthetic pyrimidine derivatives and, more particularly, to the methods of deriving the compounds that are the derivatives of 2,8-dithioxo-1H-pyrano[2,3-d: 6,5-d']dipyrimidine or its 10-aza-analogue. The compounds disclosed in the present invention are shown to possess antiviral activities against, but not limited to, the Herpes virus, the Chlamydia virus, the Influenza virus and HIV. The instant abstract is neither intended to define the invention disclosed in this specification nor intended to limit the scope of the invention in any way.

10 Claims, No Drawings

SUBSTANCE WHICH EXHIBITS ANTIVIRAL AND ANTIBACTERIAL ACTIVITY AND IS BASED ON DERIVATIVES OF 2,8-DITHIOXO-1H-PYRANO[2,3D 6,5-D']DIPYRIMIDYNE AND 10-AZA-ANALOGUE THEREOF

BACKGROUND OF THE INVENTION

1. Field of the Invention

The present invention relates generally to synthetic pyrimidine derivatives and, more particularly, to the methods of deriving the compounds that are the derivatives of 2,8-dithioxo-1H-pyrano[2,3-d: 6,5-d']dipyrimidine or its 10-aza-analogue. The compounds disclosed in the present invention are shown to possess antiviral activities against, but not limited to, the Herpes virus, the Chlamydia virus, the Influenza virus and HIV.

2. Description of the Related Art

Pyrimidine derivatives are well known biological substances active in many reactions. Synthetic derivatives, and more particularly the barbituric acids and the uracile derivatives, of pyrimidine are widely used in medicine. Research indicates that the various derivatives of 5-ilidenbarbituric acids are shown effective for the following biological activities: anticonvulsive activity, antimicrobial activity, spasmolytic activity, antipyretic activity and antitumorial activity.

High activity is also observed for the annulated derivatives of pyrimidine, e.g., pyrasole[3,4-d]pyrimidines, 5-deazaflavins, and 5-dialkylaminomethyluridines. The foregoing compounds are shown to posses a pesticide, an antitumorial, an antimicrobial, an immunosuppressive, a nootropic, an antihypertensive and an antiallergic activity.

There are still many groups of pyrimidine derivatives that are practically unstudied because of their difficulty to synthesize. There is little objective criteria that presently allows researchers to foresee the levels of the derivatives' possible activity, toxicity and side effects. In spite of these practical and theoretical drawbacks, the synthesis of and the biological activity of new pyrimidine derivatives continue to be studied. These derivatives are studied because of the considerable interest there always is in developing an effective means to treat human diseases.

Pyrano[2,3-d: 6,5-d']dipyrimidine is one of the more interesting derivatives studied. Derivatives of 5H-pyrano[2,3-d: 6,5-d']dipyrimidine are the most closely claimed compounds taken as prototypes in the present invention; however, the prototype compounds are shown to possess a limited spectrum of antiviral and antibacterial activity. They are not active against influenza viruses and they posses a low activity against retroviruses. The derivatives in the present invention, however, posses antibacterial, antiviral and immunomodulating effects.

SUMMARY OF THE INVENTION

It is an object of the present invention to provide a new and a more effective compound and one that possesses an antiviral and an antibacterial activity.

It is an object of the present invention to synthesize compounds comprising the general formula A1×M and the structural formula A1*M:

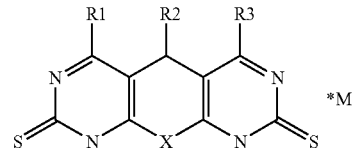

where: X is selected from the group of O, NH, N-Alkyl;

R1 is selected from the group of H, OH, Cl, O-Alkyl, $NH_2$, NH-Alkyl, NH-Ar, $N(Alkyl)_2$, SH, S-Alkyl, S-Ar, S-Hetaryl;

R2 is selected from the group of $C_6H_5$, Aryl;

R3 is selected from the group of H, Cl, O-Alkyl, $NH_2$, NH-Alkyl, NH-Ar, S-Hetaryl;

M-is absent or is selected from the group: cation Na, K, Li, ammonium or any other pharmacologically acceptable cation or complex of pharmacologically acceptable cation (see above) with anion of one of derivatives of A1 (variants R1-R3 are given above).

The best activity of claimed compounds A1*M (where M is absence) have shown the following derivatives:

| Number | X | R1 | R2 | R3 |
|---|---|---|---|---|
| Ia | O | OH | $C_6H_5$ | Cl |
| Ib | O | OH | $C_6H_4$-4-$NO_2$ | Cl |
| Iia | O | Cl | $C_6H_4$-4-$NO_2$ | Cl |
| III | O | OH | $C_6H_4$-4-$NO_2$ | $NH_2$ |
| IV | O | Cl | $C_6H_4$-4-$NO_2$ | $NH_2$ |
| V | O | $NH_2$ | $C_6H_4$-4-$NO_2$ | $NH_2$ |
| VI | NH | $NH_2$ | $C_6H_4$-4-$NO_2$ | $NH_2$ |
| VII | NH | OH | $C_6H_4$-4-Cl | $NH_2$ |
| VIII | O | OH | $C_6H_4$-4-$NO_2$ | $NHCH_3$ |
| IX | O | OH | $C_6H_4$-4-$NO_2$ | $N(CH_3)_2$ |
| X | O | OH | $C_6H_4$-4-$NO_2$ | (4,6-dihydroxypyrimidin-2-yl)thio |
| XI | O | OH | $C_6H_4$-4-$NO_2$ | H |
| XII | O | OH | $C_6H_4$-4-$NO_2$ | OH |

The following complexes were also shown to possess a high activity level:

XIII—a complex salt that consists of one mole of Ib, one mole of XII and one mole of $NH_3$;

XIV—a complex salt that consists of one mole of III, one mole of XII and one mole of $NH_3$; and XV—a complex salt that consists of one mole of XI, one mole of XII and one mole of $NH_3$.

The claimed derivatives of pyrano[2,3-d: 6,5-d']dipyrimidine A1*M can differ in prototype based on the functional group. It is therefore an object of the present invention to not limit the most active compounds and their salt-complexes to the ones shown in the table, but to disclose and to claim a method that obtains the additional compounds foreseen to possess the biological properties of the claimed compounds. It is envisioned that the most significant role in the syntheses does not belong to the structures of the R1, R2 and R3 radicals, but rather to the radicals' relevance to the chemical groups listed in the formula.

As it is seen from materials listed above, claimed derivatives of pyrano[2,3-d:6,5-d']dipyrimidine A1*M differs from prototype by other functional groups in pyrimidine fragments and can not be achieved by methods indicated in prototype. The applicant has not found sources that contained data about technical decision identical to the present invention that allows conclude that invention correspond to the criteria of "novelty" (N).

It is necessary to indicate that high biological activity of claimed compounds is not obvious from existing technical level because pyrano[2,3-d:6,5-d']dipyrimidines and 10-aza-analogues is complicated and poorly-investigated group for new members of which it is impossible to predict spectrum and activity level.

It is necessary to mention that the invention subsists not only on the most active compounds (Ia, Ib, IIa, II-XII) and their salt-complexes (XII-XV) but also on all derivatives of A1*M foreseen by invention' formula. Investigations held by us have shown that all obtained compounds synthesized by general method that is claimed by us, possess listed levels of activities. It makes possible to conclude i 5 that for synthesis and for biological properties of claimed compounds, the most significant role belongs not to the structure of R1, R2, R3 radicals but to their relevance to chemical groups listed in general formula.

No sources of information, that contained data of influence of claimed distinguishing features on achieved by their usage technical result were found by applicant. According to applicant, this fact testifies correspondence of given technical solution to criteria of "inventive step" (IS).

BRIEF DESCRIPTION OF THE TABLES

The advantages and the features of the present invention will become better understood with reference to the following more detailed description and claims taken in conjunction with the accompanying tables, in which like elements are identified with like symbols, and in which:

TABLE 1 shows the spectrums of the Paramagnetic Resonance property of the claimed compounds synthesized in the present invention;

TABLE 2 shows the decomposition points and an elemental analysis of the properties of the claimed compounds synthesized in the present invention;

TABLE 3 shows the effects of the claimed compounds on the Herpes Virus;

TABLE 4 shows the effects of the claimed compounds on Chlamydia trachomatic;

TABLE 5 shows the activity of the compounds against the influenza virus;

TABLE 6 shows the antiviral activity of the compounds against HIV; and,

TABLE 7 shows the antiviral activity of the compounds against HIV when the compounds were used in combination with other anti-HIV compounds.

DESCRIPTION OF THE PREFERRED EMBODIMENTS

The best mode for carrying out the invention is presented in terms of its preferred embodiment, herein depicted within the Tables.

A. Synthesis and the Analysis Data of the Claimed Compounds

The proposed method and the syntheses of the claimed compounds consist of two stages. In the first stage, the 5-aryl derivatives 4-chlorine-6-hydroxi-5-aryl-5,9-dihydro-1H-pyrano[2,3d: 6,5-d']dipyrimidine-2-8-dition (hereinafter "IIb") or 4,6-dichlorine-1H-pyrano[2,3-d: 6,5-d']dipyrimidine-2,8-dition ("hereinafter "IIa") are synthesized from a corresponding aromatic aldehyde and 2-thiobarituric acid. The derivative is subsequently processed by POCl$_3$ or another chlorinating and de-chlorinating agent. The first stage produces the intermediate compounds, Ia, Ib, IIa and their analogues. The intermediate compounds possess a high level of biological activity.

In the second stage, relevant compounds are synthesized using the intermediate compounds received from the first stage syntheses. The relevant compounds comprise the group III-V, VIII-XII and their analogues, wherein X=O, R1=OH, a substituted or a non-substituted group, R2 is a substituted or a non-substituted benzoic ring and R3 is a substituted or a non-substituted amino group, alkoxy group, or mercapto group. The synthesis is accomplished by substituting one or two atoms of chlorine in the intermediate tricyclic 1H-pyrano[2,3-d: 6,5-d']dipyrimidine-2,8-ditione system on the NH$_2$-, alkylamino- or the dialkylamino group, the akkoxy group, the SH-, the alkythio-, the arylthio- or the hetarylthio group with specific nucleophilic reagents (amines, alcoholates or thiolates).

New relevant compounds are synthesized from the intermediate compounds received from the first stage of the syntheses. The new relevant compounds comprise VI, VII and their analogues, wherein X=NH or X=N-Alkyl, R1=OH, a substituted or a non-substituted amino group, R2 is a substituted or a non-substituted benzoic ring and R3 is a substituted or a non-substituted amino group. The synthesis is accomplished by substituting one or two atoms of chlorine in the intermediate tricyclic 1H-pyrano[2,3-d: 6,5-d']dipyrimidine-2,8-ditione system on the NH$_2$- or the alkylamino group with the simultaneous exchange of the pyranic Oxygen atom (O10) on the amino group.

The relevant compound XI and its analogues is synthesized from the intermediate compound Ia by reductive dehalogenation to form XI and its analogues, wherein R2- is a substituted or a nonsubstituted benzoic ring.

The relevant complex salt XIII-XV is Synthesized by dissolving equimolar quantities of the compounds II, XII or XI, XII or Ib, and XII in the excess of ammonia and subsequently acidifying the solution.

EXAMPLE 1

Example 1 shows the synthesis of the intermediate product Ia, 4-chlorine-6-hydroxi-5-aryl-5,9-dihydro-1H-pyrano[2,3d: 6,5-d']dipyrimidine-2,8-dition, formed in the first stage.

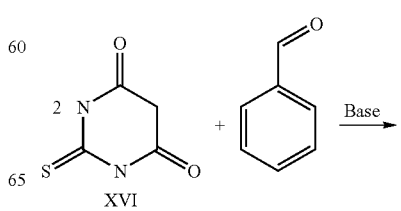

XVI

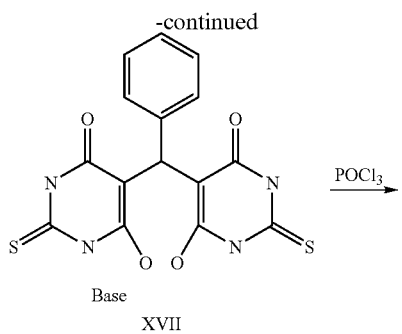

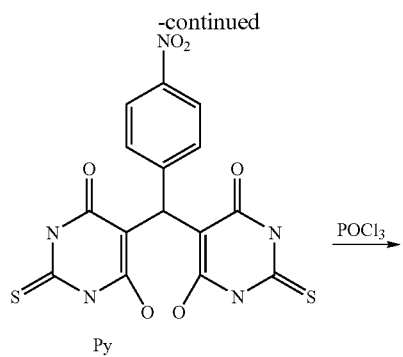

0.1 mole of 2-thiobarbituric acid (XVI) was dissolved in 50 ml of dimethylacetamide. A mixture of 0.05 mole of benzaldehyde and 0.05 mole of base (triethylamine) in a dimethylacetamide solution was added to the former solution. Ether was added several hours later. The sediment was washed by ether and dried by tetraethylammonium salt (XII). 0.3 mole of $POCl_3$ and 100 ml of chloroform were added to 27 grams of the received salt (XII). The resultant mixture was boiled for 3 hours. After the solvent was distilled, warm water was added to the residue. The solid substance was separated, washed with water and dried. The foregoing steps yielded approximately 81% of the Ia.

Note—The use of nitrobenzolealdehyde instead Of $POCl_3$ in the same technique resulted in an 8% yield of the intermediate product Ib, 4-chlorine-6-hydroxi-5-(4-nitrophenyl)-5,9-dihydro-1H-pyrano[2,3-d: 6,5-d']dipyrimidine-2,8-dition and a 7% yield of the intermediate product Ic, 4-chlorine-6-hydroxi-5-aryl-5(4-chlorphenyl)-5,9-dihydro-1H-pyrano[2,3-d: 6,5-d']dipyrimidine-2,8-dition.

Note—the use of another aromatic aldehyde instead of the $POCl_3$ results in the corresponding 5-arylderivatives 4-chlorine-6-hydroxi-5,9-dihydro-1H-pyrano[2,3-d: 6,5-d']dipyrimidine-2,8-dition, wherein X=O, R1=OH, R2=Aryl, R3=Cl and M is absent.

EXAMPLE 2

Example 2 shows the synthesis of the intermediate product IIa, 4,6-dichlorine-5-(4-nitrophenyl)-5,9-dihydro-1H-pyrano[2,3-d: 6,5-d']dipyrimidine-2,8-dition, formed in the first stage.

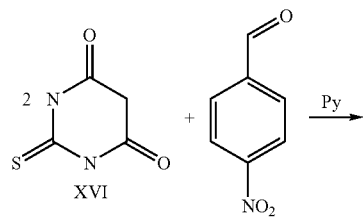

0.1 mole of 2-thiobarbituric acid (XVI) was dissolved in 50 ml of pyridine and 0.05 mole of p-nitrobenzolealdehyde. The mixture was heated up to fully dissolve the reagents. Ether was added several hours later. The sediment was washed by ether and pyridine acid and dried to form the complex salt XVIII.

26.5 grams of the received salt XVIII and 0.5 mole of $POCl_3$ were added and heated with a reflux condenser for one hour until the total solution was a sediment. The excess $POCl_3$ was distilled, water was added and the deposit precipitation was separated, washed by water and dried. 0.5 mole of $POCl_3$ was added to this compound again and the foregoing procedure was repeated. After the resultant product was washed and dried, 77% of IIa was yielded.

Note—The use of trifluoracetic acid anhydride instead of $POCl_3$ in the same technique resulted in the corresponding 4,6-hydroxi-5,9-dihydro-1H-pyrano[2,3-d: 6,5-d']dipyrimidine-2,8-dition and its analogues, wherein X=O, R1=R3+OH, R2=Aryl, and M is absent.

EXAMPLE 3

Example 3 shows the synthesis of the product III, 4-amino-6-hydroxi-5-(4-nitrophenyl)-5,9-dihydro-1H-pyrano[2,3-d: 6,5-d']dipyrimidine-2,8-dition, formed in the second stage.

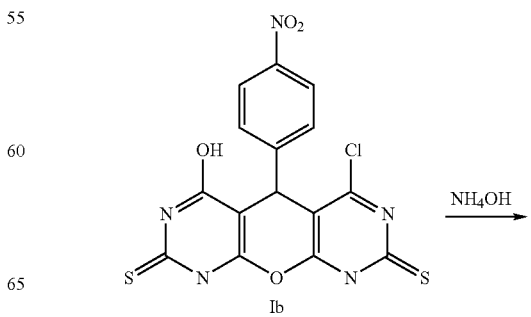

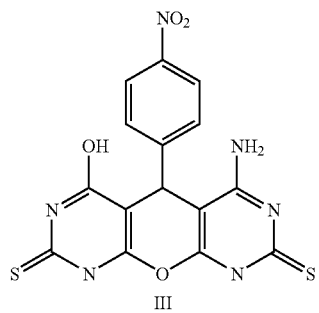

III 0.01 mole of compound 1b was mixed and diluted in 30 ml of 25% ammonia. The compound that did not dissolve in the solution was separated from the solution and the solution was stored at room temperature for 24 hours. The solution was then diluted by water and acified up to a 5-6 pH. The separated sediment was washed with water, spirit and dried. The foregoing synthesis yielded 81% III.

Note—The use of methylamine instead of ammonia in the same technique resulted in a 78% yield of the product VII, 4-methylamino-6-hydroxi-5-(4-nitrophenyl)-5,9-dihydro-1H-pyrano[2,3d: 6,5-d']dipyrimidine-2,8-dition, and a 73% yield of the IX, 4-dimethylamine-6-hydroxi-5-(4-nitrophenyl)-5,9-dihydro-1H-pyrano[2,3-d: 6,5-d']dipyrimidine-2,8-dition.

Note—The variants received from the method described in example 3 are not limited to the ones listed. The method is a general one that results in 5-aryl-4-amino derivatives 6-hydroxi--5,9-dihydro-1H-pyrano[2,3-d: 6,5-d']dipyrimidine-2, 8-dition, wherein X=O, R1=OH, R2=a substituted or a non-substituted phenyl and other aryl, R3=NH$_2$ or NHAlk and NAlk$_2$, and M is absent.

EXAMPLE 4

Example 4 shows the synthesis of the product IV, 4-chlorine-6-amino-5-(4-dinytrophenyl)-5,9-dihydro-1H-pyrano[2,3-d: 6,5-d']dipyrimidine-2,8-dition, formed in the second stage.

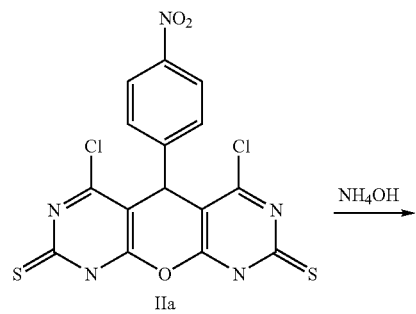

IIa

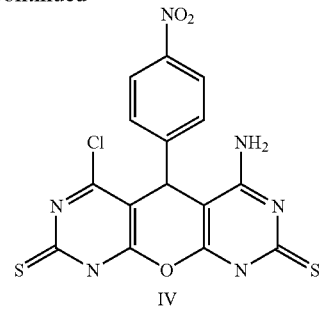

IV 10 ml of an ethanol that contained 0.02 moles of NH$_4$OH was added to and mixed with 0.01 mole of compound IIa. The mixture was incubated for 24 hours at room temperature. Then, the mixture was diluted with water and acidified to a 5-6 pH. The deposit precipitation was separated, washed by water and dried. The foregoing steps yield 54% of product IV.

EXAMPLE 5

Example 5 shows the synthesis of the product V, 4,6-diamino-5-(4-nytrophenyl)-5,9-dihydro-1H-pyrano[2,3-d: 6,5-d']dipyrimidine-2,8-dition, formed in the second stage.

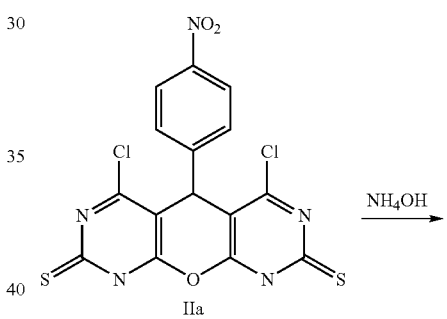

IIa

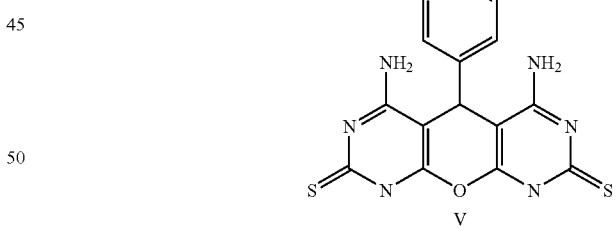

V 0.01 mole of compound IIa was mixed into and diluted with 30 ml of 25% ammonia. The compound that didn't dilute was separated. The resultant solution was incubated at room temperature, diluted with water and acidified to a 5-6 pH. The sediment was separated, washed by water, spirit and dried. The foregoing steps yielded 66% of product V.

Note—The variants received from the method described in example 5 are not limited to the ones listed. The method is a general one that results in 5-aryl derivatives of 4,6-dichlorine-5,9-dihydro-1H-pyrano[2,3-d: 6,5-d']dipyrimidine-2,8-dition in the cases when chlorine atoms substitute the ammonia in the reaction. When alkylamines are substituted for the amino groups, the 5-aryl-4,6-diaminoderivatives 5,9-dihydro-1H-pyrano[2,3-d: 6,5-d']dipyrimidine]-2,8-dition are received, wherein the general formula comprises X=O, R1 and R3=NH₂, NHAlk or NAlk₂, R2 is a substituted or a non-substituted phenyl or another aryl, and M is absent.

EXAMPLE 6

Example 6 shows the synthesis of the product VI, 4,5-diamino-10-(4-nytrophenyl)-9,10-dihydro-1H,8H-1,3,6,8,9-pentaazaantrecen-2,7dition, formed in the second stage.

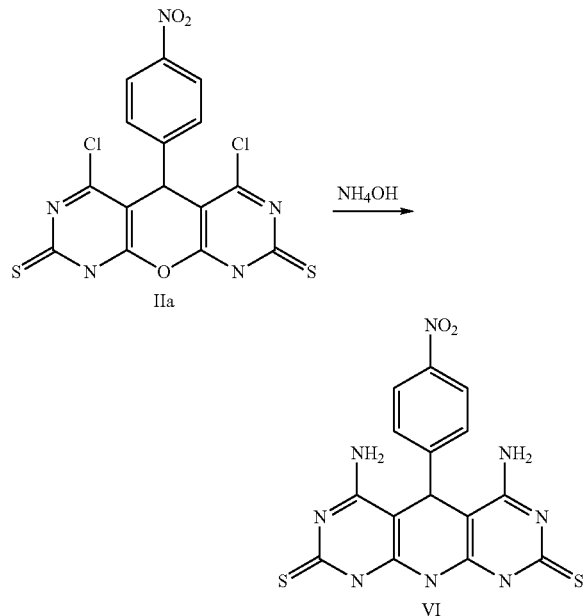

0.01 mole of compound IIa was mixed into and diluted in 80 ml of 25% ammonia. The particles that didn't dilute were filtered from the solution and the solution was heated for 24 hours by means of a reflux condenser. Then, the solution was boiled until it acquired a 40 ml volume. The solution was cooled, washed with ethanol and dried. The foregoing steps yielded 31% of product VI.

Note—The use of compound Ic instead of compound IIa in the same technique resulted in the product VII, 4-hydroxi-5-amino-10-(4-chlorphenyl)-9,10-dihydro-1H8H-1 ,3,6,8,9-pentaazaantrecen-2,7-dition.

EXAMPLE 7

Example 7 shows the synthesis of the product X, 4-(4,6-dihydroxipirimidine-2sulfanil)-6-hydroxi-5-(4-nytrophenyl)-5,9-dihydro-1H-pyrano [2,3-d: 6,5-d']dipyrimidine-2,8-dition, formed in the second stage.

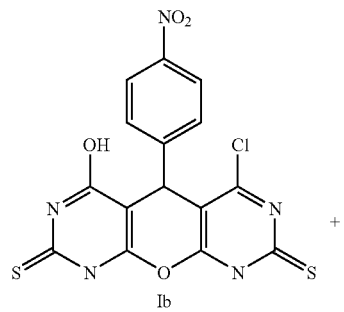

+

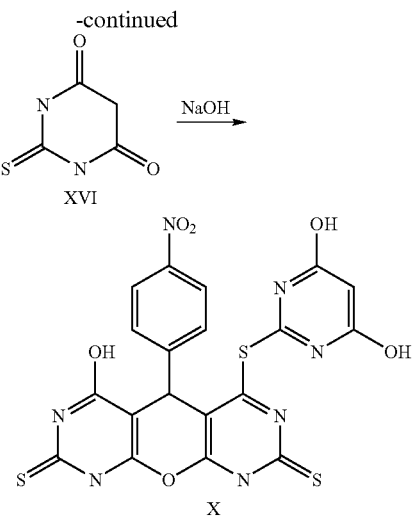

0.015 mole of 2-thiobarbituric acid (XVI) was added to 20 ml of water that contained 0.03 mole of NaOH, during which the solution was continuously mixed. 20 ml of dimethyl sulfoxide was added to the received solution. 0.01 mole of compound 1b was added. The received solution was mixed for several hours at room temperature. The solution was diluted with water and acidified to a 5-6 pH. The deposited precipitation was filtered out and the solution was washed with water, ethanol and dried. The foregoing steps yielded 42% of product X.

EXAMPLE 8

Example 8 shows the synthesis of the product XI, 6-hydroxi-5-4-(4-nitrophenyl)-5,9-dihydro-1H-pyrano[2,3-d: 6,5-d']dipyrimidine-2,8-dition, formed in the second stage.

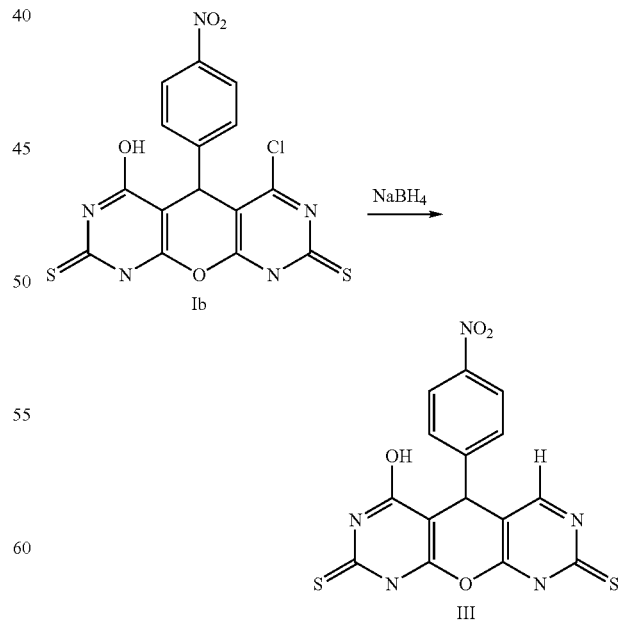

0.01 mole of compound 1b was diluted in 25 ml of concentrated acetic acid. 0.02 mole of NaBH₄ was fractionally added to the solution during 0.5 hours at a temperature no greater than 30° C. The solution was mixed for 4 hours and poured in water. The deposited precipitation was filtered and washed with water and ethanol. Then, dimethylformamide was used for recrystallization. The foregoing steps yielded 36% of product XI.

EXAMPLE 9

Example 9 shows the synthesis of the complex salt XIII, which consists of 1 mole of compound Ib, 1 mole of compound XII, and 1 mole of $NH_3$, formed in the second stage.

0.01 mole of compound Ib and 0.01 mole of compound XII were continuously mixed and diluted in 200 ml of 0.5% ammonia. This was accomplished without heat. The precipitate that did not dilute was filtered out and processed with a new portion of 50 ml of 0.5% ammonia. The united, transparent solution was acidified with acetic acid and incubated for several hours at room temperature. The deposited precipitation was filtered out and washed with water, ethanol and dried. The foregoing steps yielded 80% of product XII.

Note—Using the same technique, the complex salt XIV was received by utilizing compound II instead of compound Ib. The complex salt XV was received by utilizing compound XI instead of compound Ib.

EXAMPLE 10

Example 10 shows the synthesis of the complex salt XIV, which consists of 1 mole of compound III, 1 mole of compound XII, and 1 mole of $NH_3$, formed in the second stage.

12 ml of $POCl_3$ were added to 0.01 mole of pyridine salt XVII (See Example 2) and heated by means of a reflux condenser for 40-50 minutes until the main precipitate would not get into the solution. The solution was decantined from the precipitate. 5 ml of $POCl_3$ was distilled and poured into ice. The deposit precipitation was distilled and washed with water. 40 ml of water and 10 ml of concentrated ammonia was added to the received product and the resultant product was mixed for four hours over no heat. Most of the precipitate was diluted. The solution was filtered and acidified with acetic acid. Several hours later, the sediment was filtered, washed with water and dried. The foregoing steps yielded 71% of product XIV.

B. Experimental Determination for he Biological Effects of the Claimed Compounds The foregoing examples of the practical syntheses combined with the physical and the chemical characteristics, shown in TABLES 1 and 2, of the compounds that resulted from the syntheses confirm that the claimed compounds can be synthesized by utilizing the laboratory and the industrial means well known in the pharmaceutical industry. The present invention further confirms that the claimed compounds can be clearly identified when synthesized using the controlled methods taught herein.

In the present tests, the antiviral activity of the compounds were tested by means of administering the compounds to no-breed white mice. The compounds were administered orally (1000 mg/kg) or intraperitoneally (200 mg/kg) to mice having a mass approximating 20-25 grams. Each group of mice consisted of five males and five females. The mice were observed for a period of 14 days. There was no weight loss, changes in behavior or changes in the external appearance of the mice during the periods observed. There additionally were no toxic effects or deaths observed. The observations conclude that the claimed compounds do not possess any acute toxicity for the models tested.

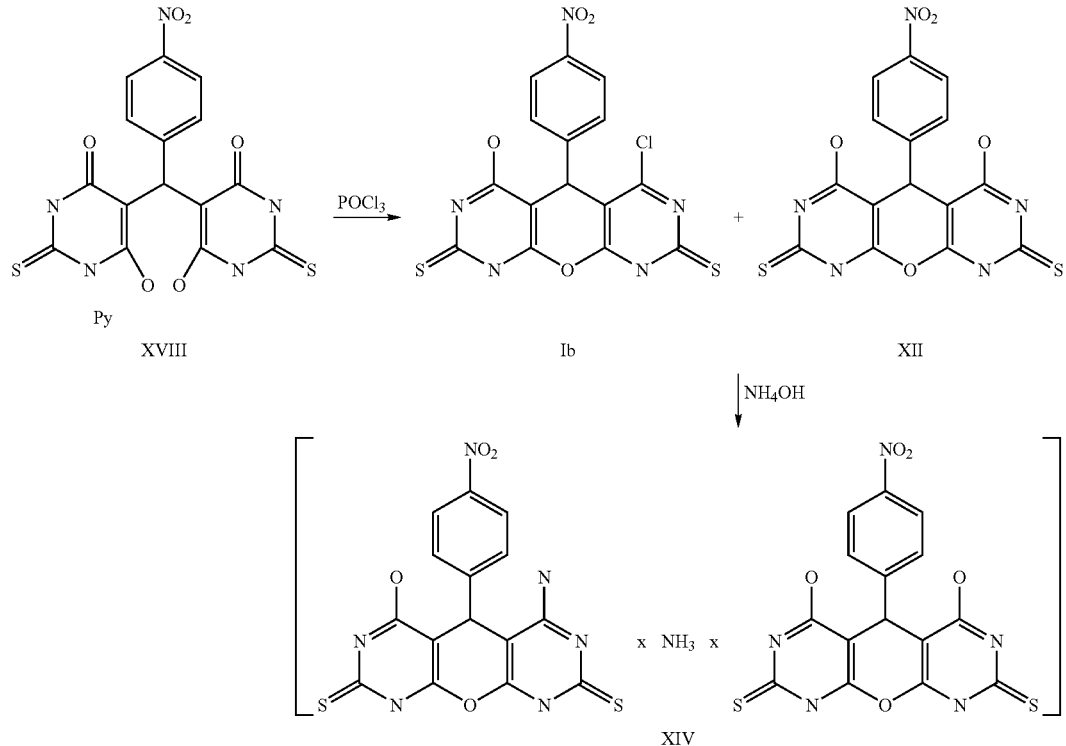

The antiviral activity of the claimed compounds were all tested against the Herpes Virus. The compounds were more specifically tested against the Herpes virus of type I by means of a generally accepted method. The viruses were grown on a continuous culture of Vero cells that were received from a bank of cell cultures. TABLE 3 charts the effects of the claimed compounds on the virus. The effects charted includes the percent of cells tested that were protected from the virus. TABLE 3 indicates that all of the claimed compounds possess activity against the virus.

The antiviral activity of the claimed compounds were also all tested against the Chlemydia trachomatis. The effects of the claimed compounds on the Chlamydia trachomatis are charted in TABLE 4. A relative strain of Chlamydia trachomatis D323 was used to test the claimed compounds. The strain, derived from a patient with Chlamydia urethritis, comprised a morphology and a physiological activity characteristic of and representative of that type. An infection dose of Chlamydia having a concentration of 1/106 cells/ml was introduced into a cell culture. Immunofluorescence (MicroTrack Chlamydia trachomatis Direct Specimen Test) was conducted to determine the significance of the chlamydial cytoplasmatic inclusions (CPI). A CylaMonoScreen was conducted to obtain the chlamydia antigens. The monolayer state and the number of cells with CPI were compared to the control to determine the effects the claimed compounds have on the chlamydia. The number of unchanged cells in 100 visual fields were counted utilizing a special net on a microscopic eyepiece.

The data charted in TABLE 4 evidences the fact that the claimed compounds can be applied to the treatment of diseases caused by chlamydia viruses.

The antiviral activity of the claimed compounds were also tested against the influenza virus. The compounds were diluted in a media and, more specifically, on a model for the chorion-allantois membrane. They were injected in wells with fragments of the chorion-allantois membrane. After the virus was added, the plates were incubated at 33° C.-34° C. for 48 hours (for the type A virus) and for 72 hours (for the type B virus). Inhibition of viral activity for the tested compounds was estimated by means of a heamagglutinating reaction (HA), that is adding 1% of chicken erythrocytes in the culture medium. The compounds' efficiency was estimated by comparing the decrease in viral activity to the control, i.e., the index of neutralization (IN). The comparisons are shown in TABLE 5. The compounds are thought to be ineffective when the IN was less than 1.0, but effective when the IN was between 1.0 to 2.0 or greater.

The results documented in TABLE 5 evidences that the claimed compounds are active against influenza viruses Type A and Type B.

Activity against the Human immunodeficiency Virus (HIV) was also determined and, more specifically, the compounds antiviral effectiveness in protecting the T-lymphoblastoid cells MT4 from being infected by the virus-containing liquid of HTHIV27 cultures. The cells infected by the virus were analyzed according to the following methods: (1) An indirect immunofluorescence (IFA) with a polyclonal anti-serum was received from an HIV Infected human (the antibody titer in the IFA was 1:1000000) and, (2) A competitive IFA was utilized with monoclonal antibodies (MonAb) to p24 HIV and a polyclonal substrate. A solution of 1:540 was used in the tests. Azidothymidin (AZT) was used as the control.

The results documented in the table shown in TABLE 6 evidence that the compounds tested inhibit the reproduction of the Human Immunodeficiency Virus Type 1.

The claimed compounds were also combined with other anti-HIV compounds and, more specifically Azidothymidin, and tested. The combined effects were estimated by measuring the cells' defence when the claimed compounds were used with azidothymidin, compounds antiviral effectiveness in protecting the T-lymphoblastoid cells MT4 from being infected by the virus-containing liquid of HTHIV27 cultures. The methods utilized to analyze the compounds effectiveness were the same as the foregoing methods.

The results documented in the table shown in TABLE 7 evidence that the compounds tested inhibit the reproduction of the Human Immunodeficiency Virus when they are combined with Aziodothymidin.

TABLE 1

| | | PMR spectra of solutions of the claimed compounds, in DMSO-d6 (δ, ppm, J, Hz) | | |
|---|---|---|---|---|
| No | C(5)H 1H, c* | Ar | NH (OH) es | $NH_2$ (NMe) Es |
| Ia | 5.02 | 6.79(1H, t), 7.16(2H, t), 7.33(2H, d)J 8.0 | 11.05(1H), 12.44(1H), 13.55(1H) | — |
| Ib | 5.03 | 7.54(2H, d)8.02(2H, d), J 8.4 | 11.18(1H), 12.35(1H), 13.40(1H) | — |
| Ic | 5.01 | 7.14(2H, d)7.45(2H, d), J 8.4 | 11.11(1H), 12.20(1H), 13.35(1H) | — |
| IIa | 5.39 | 7.56(2H, d)8.04(2H, d), J 8.3 | 12.91(2H) | — |
| III | 4.94 | 7.50(2H, d)7.92(2H, d), J 8.3 | 11.80(2H), 12.84(1H) | 11.96(2H) |
| IV | 5.10 | 7.52(2H, d)8.00(2H, d), J 8.0 | 12.70(2H) | 12.25(2H) |
| V | 4.99 | 7.48(2H, d)7.89(2H, d), J 8.2 | 12.84(2H) | 11.90(4H) |
| VI | 4.54 | 7.52(2H, d)8.00(2H, d), J 8.4 | 12.90(3H) | 11.66(4H) |
| VII | 4.66 | 7.16(2H, d)7.33(2H, d), J 8.0 | 11.15(1H), 12.91(2H) | 12.34(2H) |
| VIII | 4.85 | 7.52(2H, d)8.04(2H, d), J 8.4 | 11.20(1H), 12.45(3H) | 3.59(3H, s) |
| IX | 4.95 + 5.19 | 7.65(2H, d), 7.86(4H, m), 8.07(2H, d), J 8.0 | 11.10(2H), 12.85(3H) | — |
| X | 4.92 s | 5.28(1H, s), 7.56(2H, d) 8.04(2H, d), J 8.1 | 11.23(1H), 12.35(4H) | — |
| XI | 5.02 | 7.55(2H, d)7.97(2H, d), 8.31(1H, s) | 11.14(1H), 12.80(2H) | — |
| XII | 4.75 | 7.65(2H, d)8.11(2H, d), J 8.0 | 12.55(2H), 13.9(2H, es) | — |
| XIII | 4.80 es 5.25 es | 7.55(4H, es)8.10(4H, es) | 9.11(1H es), 11.05(2H, es); 12.45(2H, es) | 7.25(4H es) |
| XIV | 4.95 es 5.13 es | 7.53(4H, es)8.12(4H, es) | 10.00-13.50(5H, es) | 7.24(4H es) |
| XV | 4.95 es 5.13 es | 7.50(4H, es)8.07(4H, es); 8.35(1H, es) | 9.70-13.40(5H, es) | 7.25(4H es) | s—singlet, es—extended singlet, d—doublet, t—triplet, m multiplet

TABLE 2

Decomposition points, and element analysis data of the claimed compounds.

| No | T decompos., °C. | Found, % C | H | Cl | N | S | gross formula | calculated, % C | H | S | Cl | N |
|---|---|---|---|---|---|---|---|---|---|---|---|---|
| Ia | 230 | 47.90 | 2.47 | 9.33 | 14.55 | 17.19 | $C_{15}H_9ClN_4O_2S_2$ | 47.81 | 2.41 | 9.41 | 14.87 | 17.02 |
| Ib | 230 | 42.56 | 1.98 | 8.23 | 16.32 | 15.14 | $C_{15}H_8ClN_5O_4S_2$ | 42.71 | 1.91 | 8.40 | 16.60 | 15.20 |
| Ic | 245 | 43.65 | 1.99 | 17.08 | 13.46 | 15.43 | $C_{15}H_8Cl_2N_4O_2S_2$ | 43.81 | 1.96 | 17.24 | 13.62 | 15.59 |
| IIa | 240 | 40.71 | 1.55 | 15.92 | 15.88 | 14.34 | $C_{15}H_7Cl_2N_5O_3S_2$ | 40.92 | 1.60 | 16.10 | 15.91 | 14.56 |
| III | 290 | 44.49 | 2.56 | — | 20.73 | 15.67 | $C_{15}H_{10}N_6O_4S_2$ | 44.77 | 2.50 | — | 20.88 | 15.94 |
| IV | 220 | 43.31 | 2.24 | 8.30 | 19.64 | 15.04 | $C_{15}H_9ClN_6O_3S_2$ | 42.81 | 2.16 | 8.42 | 19.97 | 15.24 |
| V | 300 | 44.99 | 2.90 | — | 24.48 | 15.56 | $C_{15}H_{11}N_7O_3S_2$ | 44.88 | 2.76 | — | 24.42 | 15.97 |
| VI | 300 | 45.23 | 3.14 | — | 27.90 | 15.89 | $C_{15}H_{12}N_8O_2S_2$ | 44.99 | 3.02 | — | 27.98 | 16.01 |
| VII | 300 | 45.67 | 2.68 | 8.94 | 17.75 | 16.22 | $C_{15}H_{10}ClN_5O_2S_2$ | 45.98 | 2.57 | 9.05 | 17.87 | 16.37 |
| VIII | 300 | 46.02 | 2.95 | — | 20.03 | 15.24 | $C_{16}H_{12}N_6O_4S_2$ | 46.15 | 2.90 | — | 20.18 | 15.40 |
| IX | 265 | 47.90 | 3.41 | — | 19.43 | 14.69 | $C_{17}H_{14}N_6O_4S_2$ | 47.43 | 3.28 | — | 19.52 | 14.90 |
| X | 260 | 42.87 | 2.16 | — | 18.33 | 17.95 | $C_{19}H_{11}N_7O_6S_3$ | 43.10 | 2.09 | — | 18.52 | 18.17 |
| XI | 290 | 46.13 | 2.51 | — | 17.77 | 16.29 | $C_{15}H_9N_5O_4S_2$ | 46.51 | 2.34 | — | 18.08 | 16.55 |
| XII | 300 | 44.28 | 2.49 | — | 17.04 | 15.61 | $C_{15}H_9N_5O_5S_2$ | 44.66 | 2.25 | — | 17.36 | 15.90 |
| XIII | 230 | 42.22 | 2.87 | 4.04 | 18.01 | 14.87 | $C_{30}H_{22}ClN_{11}O_9S_4$ | 42.68 | 2.63 | 4.20 | 18.25 | 15.19 |
| XIV | 230 | 43.14 | 3.16 | — | 20.15 | 15.33 | $C_{30}H_{24}N_{12}O_9S_4$ | 43.68 | 2.93 | — | 20.38 | 15.55 |
| XV | 230 | 44.36 | 2.99 | — | 18.93 | 15.68 | $C_{30}H_{23}N_{11}O_9S_4$ | 44.49 | 2.86 | — | 19.03 | 15.84 |

TABLE 3

Effect of the claimed compounds on the Simple Herpes Virus.

| NN | Compound | Number of cells 100* | 50* | 10* |
|---|---|---|---|---|
| 1 | Acyclovir | —** | — | 9600*** (80%)**** |
| 2 | DMCO | 10000 | 10000 | 10000 |
| 3 | Cell control | 10000 | 10000 | 10000 |
| 4 | Ia | 10800 (90%) | 9600 (80%) | 7200 (60%) |
| 5 | Iib | 12000 (100%) | 10800 (90%) | 8400 (70%) |
| 6 | III | 12000 (100%) | 9600 (80%) | 8400 (70%) |
| 7 | IV | 9600 (80%) | 8400 (70%) | 6000 (50%) |
| 8 | V | 10800 (90%) | 9600 (80%) | 7200 (60%) |
| 9 | VI | 12000 (100%) | 10800 (90%) | 8400 (70%) |
| 10 | VII | 8400 (70%) | 6000 (50%) | 4000 (30%) |
| 11 | VII | 9600 (80%) | 8400 (70%) | 6000 (50%) |
| 12 | IX | 9600 (80%) | 8400 (70%) | 6000 (50%) |
| 13 | X | 10800 (90%) | 9600 (80%) | 7200 (60%) |
| 14 | XI | 9600 (80%) | 8400 (70%) | 6000 (50%) |
| 15 | XII | 6000 (50%) | 3600 (30%) | 1200 (10%) |
| 16 | XIV | 9600 (80%) | 8400 (70%) | 6000 (50%) |

*Concentration of claimed compounds (mg/l)
**Compound of given concentration was not tested
***number of cells in 100 fields under consideration
****the percentage of protection of cells from virus

TABLE 4

Effect of claimed substances on *C. trachomatis*

| NN | Compound | Percentage of cells' defense from *C. trachomatis*, % 100* | 30* |
|---|---|---|---|
| 1. | Ib | 80 | 60 |
| 2. | IIa | 90 | 70 |
| 3. | III | 100 | 70 |
| 4. | IV | 80 | 50 |
| 5 | V | 80 | 50 |
| 6 | VI | 80 | 50 |
| 7 | VII | 90 | 50 |
| 8 | VIII | 90 | 70 |
| 9 | IX | 80 | 50 |
| 10 | X | 100 | 60 |
| 11 | XI | 90 | 50 |
| 12 | XII | 60 | 40 |
| 13. | XIII | 80 | 60 |

*Concentration of claimed compounds (mg/l)

The data obtained give an evidence of the fact that the claimed compounds can be applied to treat diseases caused by chlamydia.

TABLE 5

Activity of claimed compounds against influenza virus.

| Compound | Index of neutralization Influenza virus A | Influenza virus B |
|---|---|---|
| IB | 0.5 | 0.5 |
| IIa | 1.5 | 1.5 |
| III | 0.5 | 1.0 |
| IV | 2.0 | 1.5 |
| V | 1.0 | 1.5 |
| VI | 20 | 1.5 |
| VII | 2.0 | 1.5 |
| VIII | 2.0 | 1.5 |
| IX | 2.0 | 1.5 |
| X | 1.5 | 1.0 |
| XI | 1.5 | 1.5 |

TABLE 6

Anti-HIV activity of claimed compounds.

| Compound | Concentration | Level of inhibition of virus reproduction (in %) |
|---|---|---|
| Ib | 100 mg/l | 100 |
|  | 50 mg/l | 90 |
|  | 5 mg/l | 70 |
| III | 100 mg/l | 100 |
|  | 50 mg/l | 90 |
|  | 5 mg/l | 70 |
| V | 100 mg/l | 100 |
|  | 50 mg/l | 100 |
|  | 5 mg/l | 90 |
| XIV | 100 mg/l | 100 |
|  | 50 mg/l | 100 |
|  | 5 mg/l | 100 |
| XV | 100 mg/l | 100 |
|  | 50 mg/l | 100 |
|  | 5 mg/l | 90 |
| КОНТрО Лb (AZT) | 100 mg/l | 100 |
|  | 50 mg/l | 100 |
|  | 5 mg/l | 100 |

TABLE 7

Inhibition of immunodeficiency virus' reproduction

| Compound | Concentration, mg/l | Level of inhibition of virus reproduction (in %) |
|---|---|---|
| Ib | 5.0 | 70 |
|  | 0.5 | 20 |
| AZT | 5.0 | 100 |
|  | 0.05 | 50 |
| Ib + AZT | 0.5 + 0.05 | 100 |
| XIV | 5 | 100 |
|  | 0.5 | 60 |
| Ib + AZT | 0.5 + 0.05 | 100 |

The invention claimed is:

1. A compound of formula A1*M

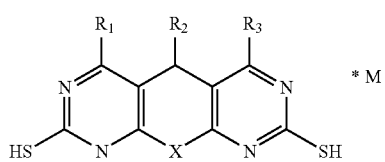

wherein X=O;
R1=OH;
R2=$C_6H_5$ or substituted phenyl: $C_6H_4X'$ (where X'=Alkyl, Halogen, $NO_2$, O-Alkyl, $N(Alkyl)_2$, CN, S-Alkyl); or disubstituted; or trisubstituted phenyl;
R3=$NH_2$; and
M is either absent or M is a cation selected from the group that consists of $Na^+$, $K^+$, $Li^+$ or $NH_4^+$.

2. A compound of formula A1*M

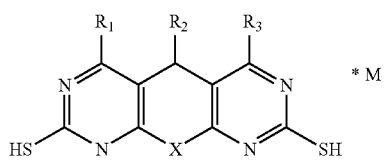

wherein X=O;
R1=Cl;
R2=$C_6H_4$-4-$NO_2$;
R3=$NH_2$; and
M is either absent or M is a cation selected from the group that consists of $Na^+$, $K^+$, $Li^+$ or $NH_4^+$.

3. A compound of formula A1*M

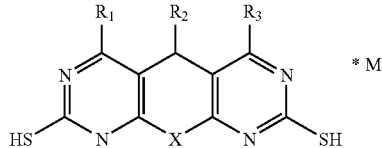

wherein X=O;
R1=$NH_2$;
R2=$C_6H_4$-4-$NO_2$;
R3=$NH_2$; and
M is either absent or M is a cation selected from the group that consists of $Na^+$, $K^+$, $Li^+$ or $NH_4^+$.

4. A compound of formula A1*M

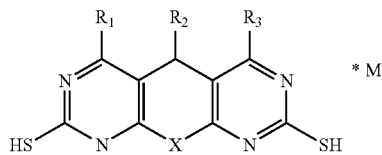

wherein
X=NH;
R1=$NH_2$;
R2=$C_6H_4$-4-$NO_2$;
R3=$NH_2$; and
M is either absent or M is a cation selected from the group that consists of $Na^+$, $K^+$, $Li^+$ or $NH_4^-$.

5. A compound of formula A1*M

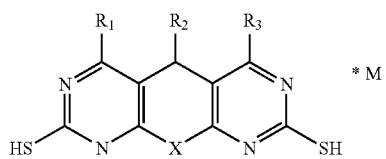

wherein
X=NH;
R1=OH;
R2=$C_6H_4$-4-Cl;
R3=$NH_2$; and
M is either absent or M is a cation selected from the group that consists of $Na^+$, $K^+$, $Li^+$ or $NH_4^+$.

6. A compound of formula A1*M

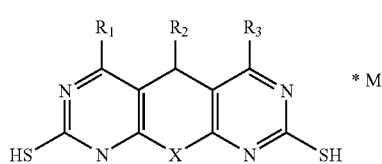

wherein
X=O;
R1=OH;

R2=C$_6$H$_4$-4-NO$_2$;
R3=NHCH$_3$; and
M is either absent or M is a cation selected from the group that consists of Na$^+$, K$^+$, Li$^+$ or NH$_4^+$.

7. A compound of formula A1*M

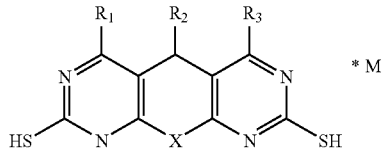

wherein
X=O;
R1=OH;
R2=C$_6$H$_4$-4-NO$_2$;
R3=H; and
M is either absent or M is a cation selected from the group that consists of Na$^+$, K$^+$, Li$^+$ or NH$_4^+$.

8. A compound of formula A1*M

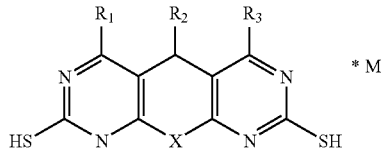

wherein
X=O;
R1=OH;
R2=C$_6$H$_4$-4-NO$_2$;
R3=Cl; and
M=CH$_3$+A1, wherein the functional groups on A1 comprise X=O, R1=OH, R2=C$_6$H$_4$-4-NO$_2$ and R3=OH.

9. A compound of formula A1*M

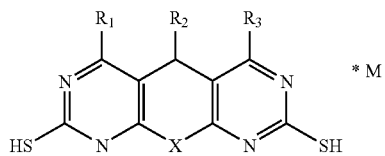

wherein
X=O;
R1=OH;
R2=C$_6$H$_4$-4-NO$_2$;
R3=NH$_2$; and
M=NH$_3$+A1, wherein the functional groups on A1 comprise X=O, R1=OH, R2=C$_6$H$_4$-4-NO$_2$ and R3=OH.

10. A compound of formula A1*M

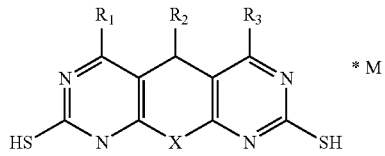

wherein
X=O;
R1=OH;
R2=C$_6$H4-4-NO$_2$;
R3=H; and
M=NH$_3$+A1, wherein the functional groups on A1 comprise X=O, R1=OH, R2=C$_6$H$_4$-4-NO$_2$ and R3=OH.

* * * * *